United States Patent [19]
Johnson

[11] Patent Number: 4,719,914
[45] Date of Patent: Jan. 19, 1988

[54] ELECTROSURGICAL INSTRUMENT

[76] Inventor: Gerald W. Johnson, 17070 Red Oak, Ste. 301, Houston, Tex. 77090

[21] Appl. No.: 946,485

[22] Filed: Dec. 24, 1986

[51] Int. Cl.⁴ ..................... A61B 17/39; A61M 1/00
[52] U.S. Cl. ..................... 128/303.1; 128/303.14; 128/303.17; 604/35
[58] Field of Search ............... 128/303.13–303.19, 128/303.1; 604/20, 22, 35

[56] References Cited

U.S. PATENT DOCUMENTS

| | | | |
|---|---|---|---|
| 2,275,167 | 3/1942 | Biermen | 128/303.17 |
| 2,376,265 | 5/1945 | Meredith | 128/303.14 |
| 2,888,928 | 6/1959 | Serger | 128/303.17 |
| 3,906,955 | 9/1975 | Roberts | 128/303.17 |
| 4,074,718 | 2/1978 | Morrison, Jr. | 128/303.14 |
| 4,307,720 | 12/1981 | Weber, Jr. | 128/303.17 |
| 4,347,842 | 9/1982 | Beale | 128/303.13 |
| 4,562,838 | 1/1986 | Walker | 128/303.14 |

FOREIGN PATENT DOCUMENTS

| | | | |
|---|---|---|---|
| 57862 | 9/1953 | France | 128/303.14 |
| 1465581 | 1/1967 | France | 128/303.18 |
| 306843 | 7/1971 | U.S.S.R. | 128/303.17 |

Primary Examiner—Lee S. Cohen
Attorney, Agent, or Firm—Neal J. Mosely

[57] ABSTRACT

An electrosurgical instrument is disclosed comprising a hollow tubular member open at one for connection by a hollow tubing to a source of vacuum and a side opening adjacent to the open end. The opposite end of the tubular member includes a tapered hollow nose portion which may be integral with the tubular member or a separate piece. An electrocauterizing blade is secured in and has one end extending outward from the end of the nose portion and the other end positioned inside the tubular member. Electric heating is provided for the electrocauterizing blade through an electric lead extending through the tubular member and through the side opening for connection to a power source. The electric heating is usually provided by application of high frequency current but may be provided by resistance heating. The nose portion has a plurality of openings adjacent to the tapered surface thereof for withdrawing smoke from a surgical area being cut and cauterized by means of vacuum connected to the end of the tubular member. Selectively control of the application of vacuum through the nose portion openings is provided by a tubular sleeve member supported for longitudinal movement on the nose portion to an extended position for selectively covering and uncovering the nose portion openings.

12 Claims, 5 Drawing Figures

U.S. Patent  Jan. 19, 1988  4,719,914
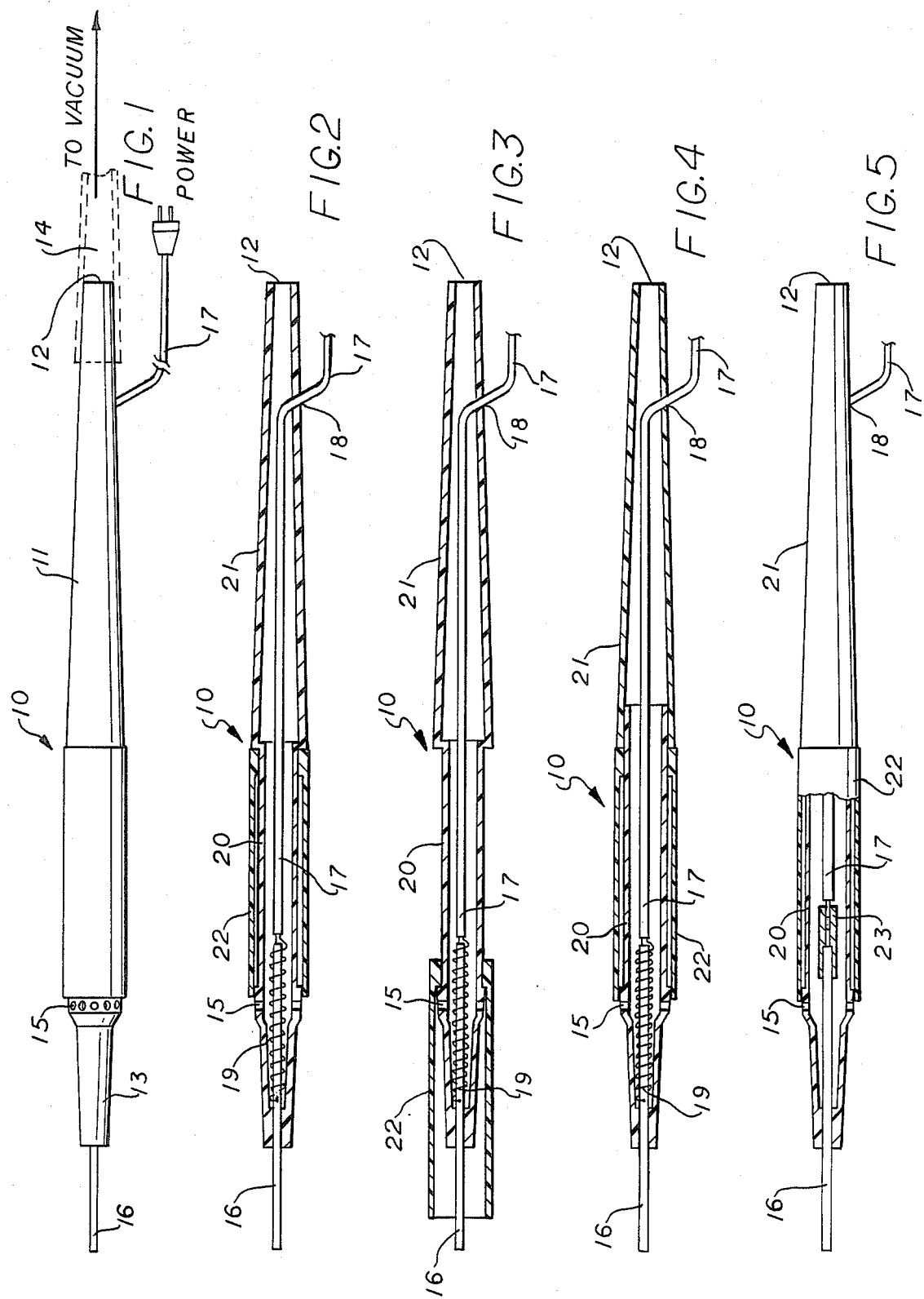

ELECTROSURGICAL INSTRUMENT

BACKGROUND OF THE INVENTION

1. Field of the Invention

This invention relates to new and useful improvements in electrosurgical instruments and more particularly to an instrument having an electro-cauterizing blade and provision for selective application of vacuum to the surgical site.

2. Brief Description of the Prior Art

Electrosurgical instruments having an electric cauterizing blade and some means for aspirating blood and/or smoke from the surgical area have been disclosed in the literature for about 50 years.

Hyams U.S. Pat. No. 2,102,270 discloses an electrosurgical instrument for female sterilization procedures having an auxiliary tube surrounding the electric blade for introduction of a liquid for radiologically monitoring the operation.

Bierman U.S. Pat. No. 2,275,167 discloses an electrosurgical instrument for removal of tissue by electric current and having means for applying vacuum for drawing in and holding the tissue being cut.

August U.S. Pat. No. 2,808,833 discloses an electro-cauterizing instrument with a tube for supplying an inert gas to blanket the surgical site.

Seiger U.S. Pat. No. 2,888,928 discloses an electro-cauterizing instrument with a tube for withdrawing blood and smoke from the surgical site by vacuum.

Morrison U.S. Pat. No. 3,828,780 discloses an electro-cauterizing instrument with a tube for withdrawing blood and smoke from the surgical site by vacuum and having a side vent opening.

Roberts U.S. Pat. No. 3,906,955 discloses an electro-cauterizing instrument with a tube for withdrawing blood and smoke from the surgical site by vacuum and constructed for easy replacement of the blade.

Durden U.S. Pat. No. 3,974,833 discloses an electro-cauterizing instrument with a tube for withdrawing blood and smoke from the surgical site by vacuum and having a side vent opening arranged for selective opening and closing to control application of vacuum.

Walker U.S. Pat. No. 4,562,838 discloses an electro-cauterizing instrument with a tube for supplying fluid to the surgical site for removing blood and smoke and having a light transmitting cable for illuminating the surgical site.

The prior art as exemplified by these patents and by the instruments now in use in surgery have certain similarities and certain deficiencies in design. All instruments of this type have an electrode for high frequency electro-coagulation. Likewise, most instruments of this type have a tube associated with the blade to either supply a liquid to the surgical site or to aspirate blood and fluid or air (smoke) away from the site. Roberts U.S. Pat. No. 3,906,955 and Walker U.S. Pat. No. 4,562,838 have superficial similarities to my invention and in certain applications work similarly. However these instruments are not as versatile and do not work well in all types of operating conditions. Roberts U.S. Pat. No. 3,906,955 discloses an electro-cauterizing instrument with a tube for withdrawing blood and smoke from the surgical site by vacuum but has a design which provides an inadequate air circulation through the tip for removal of smoke and fluids. Walker U.S. Pat. No. 4,562,838 discloses an electro-cauterizing instrument with a tube for supplying fluid to the surgical site for removing blood and smoke and having a light transmitting cable for illuminating the surgical site, but has an inefficient design of the air flow passages for removal of blood and smoke from the surgical site.

SUMMARY OF THE INVENTION

One of the objects of this invention is to provide a new and improved electro-surgical and electro-cauterizing instrument having an evacuation system of more efficient design for removal of blood and smoke from the surgical site.

Another object of the invention is to provide a new and improved electro-surgical and electro-cauterizing instrument having an evacuation system permitting selective application of vacuum during surgery.

Another object of the invention is to provide a new and improved electro-surgical and electro-cauterizing instrument having an arrangement for enclosing the surgical site to force circulation of air through that region by application of vacuum.

Still another object of the invention is to provide a new and improved electro-surgical and electro-cauterizing instrument having a hood or sleeve which is extensible to cause circulation of air through the surgical site and out through discharge openings by application of vacuum to the opposite end of the instrument.

Other objects of the invention will become apparent from time to time throughout the specification and claims as hereinafter related.

The foregoing objects and other objects of the invention are accomplished by an electrosurgical instrument comprising a hollow tubular member open at one for connection by a hollow tubing to a source of vacuum and a side opening adjacent to the open end. The opposite end of the tubular member includes a tapered hollow nose portion which may be integral with the tubular member or a separate piece. An electrocauterizing blade is secured in and has one end extending outward from the end of the nose portion and the other end positioned inside the tubular member. Electric heating is provided for the electro-cauterizing blade through an electric lead extending through the tubular member and through the side opening for connection to a power source. The electric heating is usually by application of high frequency current but may be provided by resistance heating. The nose portion has a plurality of openings adjacent to the tapered surface thereof for withdrawing smoke from a surgical area being cut and cauterized by means of vacuum connected to the end of the tubular member. Selectively control of the application of vacuum through the nose portion openings is provided by a tubular sleeve member supported for longitudinal movement on the nose portion to an extended position for selectively covering and uncovering the nose portion openings.

BRIEF DESCRIPTION OF THE DRAWINGS

FIG. 1 is a view in elevation of an electro-surgical instrument illustrating a preferred embodiment of this invention.

FIG. 2 is view in longitudinal central section of the instrument shown in FIG. 1 with the hood or sleeve retracted.

FIG. 3 is view in longitudinal central section of the instrument shown in FIG. 1 with the hood or sleeve in an extended position.

FIG. 4 is view in longitudinal central section of the instrument similar to that shown in FIG. 1, but having a two-piece construction of the tubular supporting member and blade-holding nose portion.

FIG. 5 is view in longitudinal central section of the instrument similar shown in FIG. 1, but showing an alternate electrical heater for the surgical blade.

DESCRIPTION OF THE PREFERRED EMBODIMENTS

Referring to the drawings by numerals of reference, there is shown in FIG. 1 an electrosurgical instrument 10 comprising a hollow tubular member 11 having on open rear end 12 and a tapered nose portion 13. Rear end 12 of tubular member 11 is connected, in use, by hollow tubing 14 to a vacuum pump or other source of vacuum (not shown).

The tapered nose portion 13 has a plurality of openings 15 set back a substantial distance from the end of the instrument. A cutting and cauterizing blade 16 is supported in the end of nose portion 13 and extends inside tubular member where it is connected to an electric lead 17 which extends out through an opening 18 in tubular member 11 for connection to an electric power source (not shown). In this embodiment, electric lead 17 has a resistance heater coil 19 connected to blade 16 for heating the blade to either a cutting or cauterizing temperature.

Tapered nose portion connects to a tubular portion 20 having an O.D. smaller than the O.D. of the rear portion 21 of tubular member 11. A tubular sleeve or hood member 22 is positioned for sliding movement on tubular portion 20 and has a retracted position against a shoulder formed the end of rear tubular portion 21. In the retracted position, the outer end of sleeve or hood 22 does not cover openings 15 in the tapered portion of nose portion 13. Sleeve or hood 22 is movable to an extended position as shown in FIG. 3.

In FIG. 4, tubular member 11 is formed in two parts with rear portion 21 being one part and nose portion 13 and tubular portion 20 forming the other part. In this embodiment, tubular portion 20 has an O.D. fitting tightly in the I.D. of tubular portion 21. In this embodiment, sleeve or hood 22 is slidable positioned on tubular portion 20 and has a retracted position against the shoulder formed by the end of tubular portion 21.

In FIG. 5, the electric lead 17 is connected to cutting and cauterizing blade 16 by a conventional connector 23 and is designed for use with a source of high frequency electric current. The use of high frequency electric heating for cutting and cauterizing blades is conventional in surgical instruments of this type. The instrument is operated with a lower frequency for cutting and higher frequency for cauterizing, but both frequencies are in the high frequency range.

OPERATION

The electrosurgical instrument 10 is used in surgical operations in a manner similar to the prior art instruments. The instrument is connected to a source of vacuum (not shown) by tubing 14. The electric lead 17 is connected to a power source which is preferably a high frequency electrosurgical generator, although, for some instruments using a simple electric resistance coil heater commercially available power, e.g. 110 V. 60 cycles, may be used. In either case, blade 16 is heated to one temperature for cutting and to a substantially higher temperature for cauterizing.

When the operation is being carried out with blade 16 extending into the tissue being cut, sleeve or hood 22 is used in a retracted position. If the blade is used for cauterizing, there is a substantial evolution of smoke and gases which is withdrawn through openings 15 and the interior of tubular member 11 by the vacuum applied through tubing 14. When the blade 16 is used for cutting or cauterizing in the open, sleeve or hood 22 is moved to its most extended position adjacent to the cutting end of blade 16 as in FIG. 3. In this position, sleeve or hood 22 is positioned substantially at the surgical site and defines an opening extending back to openings 15 in nose portion 13 to provide more efficient removal of smoke and gases.

It should be noted that most operating rooms are equipped with electrosurgical generators which utilize high frequency current. One frequency is used in the cut mode and the other with the coagulation mode. Most surgical procedures requiring large areas of dissection are done with the cut mode and the blade tip. When a larger blood vessel is cut or encountered, it is clamped and zapped with the coagulation mode. The smoke generated by the cutting dissection from burning or vaporizing fat and other tissue is very offensive to smell, terribly irritating to the eyes (especially to those wearing contact lenses) and is carcinogenic. Unless the smoke is constantly evacuated by a vacuum connection, it will pervade the entire room and the operating suite.

The prior art has provided vacuum systems for removing smoke from the surgical site. The volume of air moved is dependent on the pressure, diameter of the tube, and the length of the tube. Since the pressure (negative pressure or vacuum) is fairly standard in most operating rooms, e.g., 100 -250 mm. Hg, depending on the regulator setting, and since the diameter and length of most suction and connection tubing is fairly standard, the critical variables are (a) the size of the suction portion of the instrument, and (b) the proximity and configuration of the open end of the suction to the cutting tip.

Roberts U.S. Pat. No. 3,906,955 shows an instrument with suction in close proximity to the cutting tip. The openings, however, are of an inefficient configuration (located on the side) and the cross section of the suction tube is very small. Walker U.S. Pat. No. 4,562,838 shows an instrument with good cross section in the suction tube but has an inefficient configuration and is not in close proximity to the cutting tip.

If the volume of free air movement into and through the suction tube remains constant per unit time, then the effect of the vacuum at the suction tip on the surrounding free air is inversely proportional to the square of the distance from the suction tip.

In this invention, operating as described above, the calculation just discussed shows that its efficiency is substantially superior to the instrument of Roberts U.S. Pat. No. 3,906,955 and about 16 times more efficient than the instrument of Walker U.S. Pat. No. 4,562,838.

Much of this advantage arises from the use of the extended sleeve or hood 22 which moves the region of suction adjacent to the cutting tip. It is not possible to use a fixed, extended sleeve or hood because of problems of sanitation required in surgery. When an extensive operation is carried out utilizing both the cutting and coagulation modes, fat and tissue is carbonized to a residue which sticks to the cutting tip much as carbonized fats stick to and encrust a cooking grill. The cutting tip must be cleaned frequently by scraping away the carbonized organic materials. This cleaning cannot be done if a fixed, extended sleeve or hood is used. The use of the retractable sleeve or hood 22 therefore performs the dual function of increasing the suction adjacent to the cutting tip and, on retraction, permits the cleaning of the cutting tip or blade 16.

While this invention has been described fully and completely, with special emphasis on the preferred embodiments, it should be understood that, within the scope of the appended claims, the invention may be practiced otherwise than as specifically described herein.

What is claimed is:

1. An electrosurgical instrument comprising:
   a hollow tubular member having an opening at one end adapted for connection by hollow tubing to a source of vacuum, and a side opening adjacent to said one end,
   the opposite end of said tubular member including a tapered hollow nose portion,
   an electrocauterizing blade secured in and having one end extending outward from the end of said nose portion and the other end positioned inside said tubular member,
   electric heating means for said electrocauterizing blade including an electric lead extending through said tubular member and through said side opening for connection to a power source,
   said nose portion having a plurality of openings adjacent to the tapered surface thereof adapted to withdraw smoke from a surgical area being cut and cauterized by means of a vacuum connected to said tubular member open end, and
   means for selectively controlling the application of vacuum through said nose portion openings comprising means supported on said tubular member for selectively covering and uncovering said nose portion openings.

2. An electrosurgical instrument according to claim 1 in which
   said tubular member opposite end is smaller in outside diameter than said one end and the tapered nose portion commences its taper from said smaller diameter.

3. An electrosurgical instrument according to claim 2 in which
   said vacuum-controlling means comprises a tubular sleeve member supported for longitudinal movement on said smaller diameter portion.

4. An electrosurgical instrument according to claim 3 in which
   said sleeve member is imperforate and has an inside diameter permitting sliding movement on said tubular member smaller diameter portion between a retracted and an extended position, and
   the inside diameter of said sleeve member and tapered surface of said nose portion cooperating when said sleeve member is moved to an extended position to provide a passage for directing flow of smoke and gases from a cauterizing site through said nose portion openings and said tubular member when vacuum is applied thereto.

5. An electrosurgical instrument according to claim 1 in which
   said tubular member and said nose portion are of a one-piece molded plastic construction.

6. An electrosurgical instrument according to claim 1 in which
   said tubular member and said nose portion are molded of plastic material as separate pieces, said nose portion fitting inside the opposite end of said tubular member.

7. An electrosurgical instrument according to claim 1 in which
   said electric heating means for said electrocauterizing blade comprises an electrical resistance heater connected to said electric lead extending through said tubular member and through said side opening for connection to a power source.

8. An electrosurgical instrument according to claim 1 in which
   said electric heating means for said electrocauterizing blade comprises an electrical resistance member integral with said blade and connected to said electric lead extending through said tubular member and through said side opening for connection to a high frequency power source.

9. An electrosurgical instrument according to claim 1 in which
   said tubular member and said nose portion are molded of plastic material as separate pieces, said nose portion fitting inside the opposite end of said tubular member, and
   said vacuum-controlling means comprises a tubular sleeve member supported for longitudinal movement on said smaller diameter portion.

10. An electrosurgical instrument according to claim 9 in which
    said sleeve member being imperforate and having an inside diameter permitting sliding movement on said nose portion between a retracted position on said tubular member and an extended position therefrom, and
    the inside diameter of said sleeve member and tapered surface of said nose portion cooperating when said sleeve member is moved to an extended position to provide a passage for directing flow of smoke and gases from a cauterizing site through said nose portion openings and said tubular member when vacuum is applied thereto.

11. An electrosurgical instrument according to claim 13 in which
    said electric heating means for said electrocauterizing blade comprises an electrical resistance heater connected to said electric lead extending through said tubular member and through said side opening for connection to a power source.

12. An electrosurgical instrument according to claim 10 in which
    said electric heating means for said electrocauterizing blade comprises an electrical resistance member integral with said blade and connected to said electric lead extending through said tubular member and through said side opening for connection to a high frequency power source.

* * * * *